United States Patent [19]

Madray

[11] 4,324,549

[45] Apr. 13, 1982

[54] ASSEMBLY FOR ATTACHING A DENTAL PROSTHESIS TO TEETH

[76] Inventor: George W. Madray, 2525 Community Rd., Brunswick, Ga. 31520

[21] Appl. No.: 191,019

[22] Filed: Sep. 26, 1980

Related U.S. Application Data

[63] Continuation of Ser. No. 960,118, Nov. 13, 1978, abandoned.

[51] Int. Cl.³ .............................................. A61C 13/28
[52] U.S. Cl. .................................................. 433/169
[58] Field of Search ............... 433/177, 172, 193, 169, 433/170

[56] References Cited

U.S. PATENT DOCUMENTS

| | | | |
|---|---|---|---|
| 1,140,539 | 5/1915 | Skinner | 433/172 |
| 4,204,321 | 5/1980 | Scott | 433/177 |

FOREIGN PATENT DOCUMENTS 370865  9/1963  Switzerland .................. 433/172

*Primary Examiner*—Robert Peshock
*Attorney, Agent, or Firm*—Paul E. Friedemann

[57] ABSTRACT

The invention has two main parts. First, there is an assembly of elements including a prefabricated precision stud, or male element, preferably made of metal, as stainless steel for example, securely anchored by a specially designed cap fitting onto a prepared matching outer end of a tooth, and a second assembly of elements including a prefabricated thimble, or female part, preferably made of plastic material. The thimble element is provided, at its outer upper region, with burrs, or projections, so that the thimble element may be rigidly held in the denture material, but the skirt or lower region of the thimble element does not contact the denture material and may thus flex, or stretch, circumferentially, and thus expand radially, to receive the stud element with a snap action, so that the two main parts are snap retained to each other.

The thimble element should be made available in a tissue-resilient type, and somewhat more non-resilient type, to match the need, for example, in the tissue-resilient type it would be used when the denture is supported more by the gum than by the teeth, whereas in the non-resilient type it would be used when the denture is supported more by the teeth than by the gum.

The anchor provided by this invention creates a favorable crown-root ratio where there is minimal interocclusal space, approximately 3 mm. for both forms.

With this invention all fitting fabrication is performed chairside, all parts are relatively inexpensive, and are easy to service.

4 Claims, 3 Drawing Figures

ASSEMBLY FOR ATTACHING A DENTAL PROSTHESIS TO TEETH

This application is a continuation of Ser. No. 960,118 filed Nov. 13, 1978, now abandoned.

BRIEF DESCRIPTION OF THIS INVENTION IN RELATION TO PRIOR ART

When wearing dentures, particularly a lower denture, it is harder to keep in place because it does not have the "suction" fit of an upper denture. The lower denture often has to be relined because the lower ridge of bone resorbs readily if some teeth are not retained as abutments; therefore, the fit will not be as secure without the abutments.

The anchor, by being male on the abutment tooth, will in a number of cases not require any kind of endodontic therapy. In older teeth, especially where the anterior teeth are few in number and have been used extensively in mastication, they have been worn from an incisal to a gingival direction, producing pulpal resorption. When pulpal resorption has occurred, the tooth can be prepared for my attachment without having to do any kind of endodontic therapy. The anchor also crowns the tooth, holding it together to prevent splitting of the root, which is also important in teeth that have been treated endodontically. By not going inside the remaining root, the anchor does not produce weakened walls.

The Zest Anchor is an intra radicular attachment that produces walls of a weak nature. This anchor always requires endodontic therapy and, through hydraulic pressure that builds up, often causes the nylon male end to fracture; thus servicing has to be done in the mouth to remove the ball from its socket.

Other precision stud attachments consist of precious metals which cannot be fabricated chairside, and are not easy to service. Most cases involve the use of gold attachments that have to be fitted to a root coping, or crown. The dentist thus has to assess a fee to pay for crowning, to compensate a lab technician, and to pay for the gold stud.

OBJECTS OF THE INVENTION

It is an object of this invention, for anchorage, to create cap-structures on retained teeth. While this procedure lowers crown-root ratio, it will create anchorage for overdentures and partial dentures to retained abutment teeth. This produces a more stable denture, and one which will give longer service.

It is an object of this invention to "cap" or "crown" the remaining root of the abutment tooth, or teeth. This procedure prevents the abutment from having weakened walls, and if endodontic therapy has to be done, it prevents the root from splitting.

It is another object of this invention to provide an inexpensive way to deliver a better sevice by the dentist, for anchorage of dentures, because the invention can be fabricated in the office of inexpensive material for a very reasonable price. Thus, the patient with only several remaining teeth will be more reasonable in accepting the treatment plan, and will be kept from becoming a dental cripple.

Another object of this invention is to provide a protective seal over the pulp canal when a mechanical pulp cap is tried without putting pressure on the pulp canal itself. (There is substantial evidence showing different mixing of medicaments that will produce secondary reparative dentinal formation in pulp capping.)

Another object of this invention is to provide some resilience in the anchorage, particularly in the vertical direction, so not all of the load from mastication is put just on the abutment teeth. By having the male portion of the attachment on the tooth, the area on the denture that would normally put pressure on the abutment by way of the male portion of the attachment, can be relieved even after the denture is built. This is desirable because some support should come from the tissue.

A further, somewhat more specific object of this invention, is that the flange of the male portion of the attachment is over solid tooth structure, and is of sufficient area to provide a partial cap for the tooth and pins are used on the flange projecting down into the tooth to prevent the attachment from rotating on the root of the tooth, which would cause the cement seal to break after that portion of the attachment is cemented.

Other objects and advantages of this invention will become apparent from a study of the following description and a study of the details of the accompanying drawings, wherein.

Figure 1:
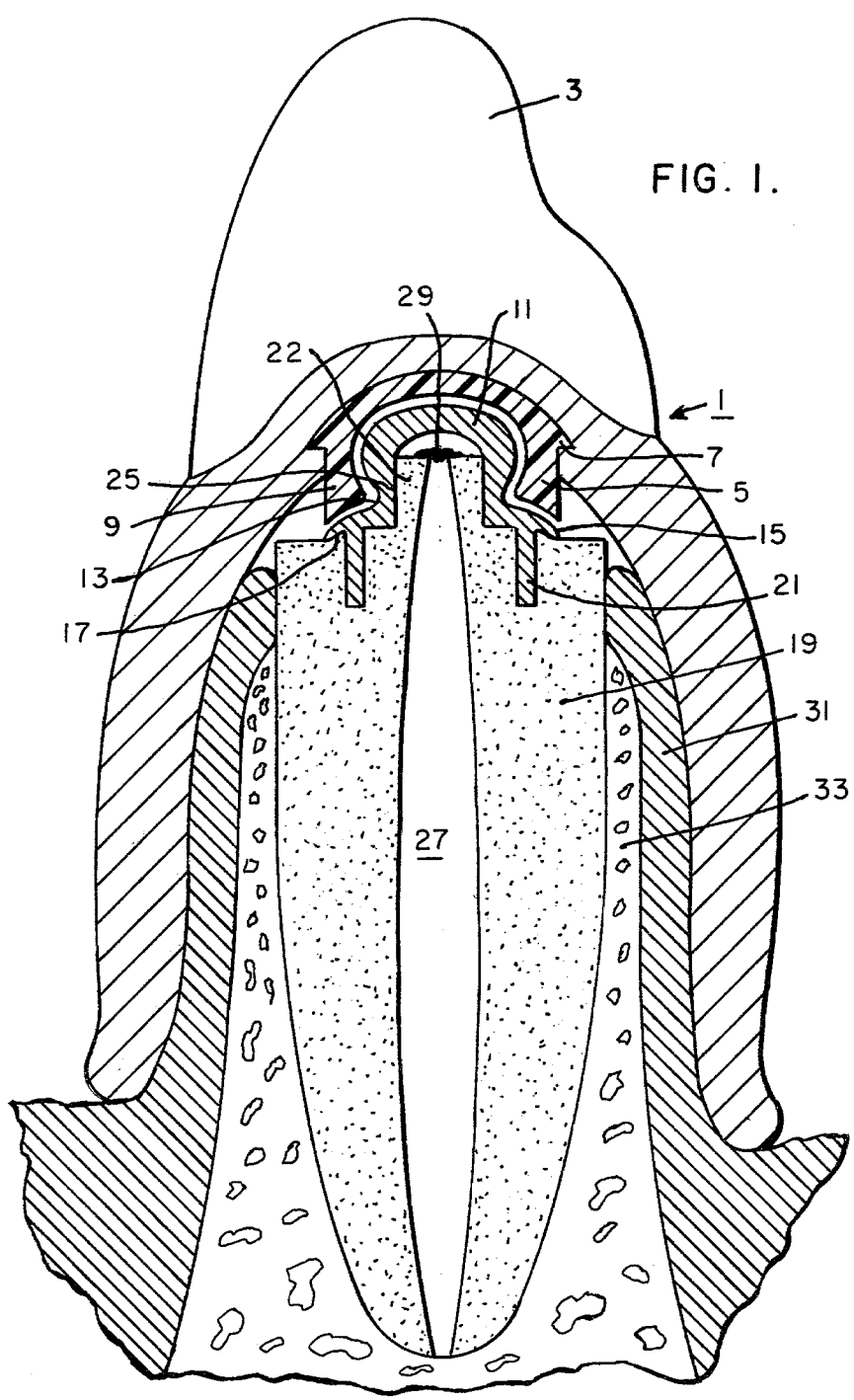
FIG. 1 is an enlarged cross-sectional view on a vertical plane at a right angle to the lower human jawbone, and shows a fragmentary view of an anterior section of a denture, in use, in the mouth.

In FIG. 1, the anchorage structure is shown in place under the denture 1. The denture tooth 3, not shown in section, sits on top of the denture and is securely attached thereto. The thimble, or female, element 5 is, at its top, embedded in the denture 1, and is securely held in the denture by the retaining means 7. The retaining means 7 may comprise a latch ring, as shown, or a plurality of circumferentially spaced latch projections. The retaining means 7 precludes the possibility of any rotation of element 5 in the denture 1, should the dentist find a need to work on the inner surface of element 5. The skirt portion 9 of thimble element 5 does not touch the denture 1, and, being made of resilient plastic material, may thus be stretched sufficiently to receive the stud, or male, element 11 to the position shown with a snap action.

The stud element 11 has:

An upper spheroidal end with its greater diameter disposed in a horizontal plane and having a dimension to fit, somewhat loosely, into the spheroidal inner upper region of the thimble element;

A constricted mid-region 13 having a horizontal outside diameter of slightly lesser dimension than the inner horizontal diameter of the skirt portion 9;

A base structure provided with a load receiving upper surface 15 co-acting with the lower end of the skirt element to take some load during use; and A lower surface 17, directed toward the apex as opposed to being flat, forming the all-important cap for the tooth 19, and has pins 21 providing circumferential anchorage for the stud element.

The inner region of the stud element 11 has a cylindrical hollowed-out region 25 to snugly receive the cylindrical upper tooth end 22 surrounding the pulp canal 27, providing retention. Room is provided at the tooth end 22 for the pulp capping medicament 29.

Since the stud element 11 fits rather loosely into the thimble element 5 and the space surrounding the skirt portion 9 is void, it is apparent that the denture 1 gets some support from the gums 31 as well as the tooth 19 and the jaw bone 33.

Figure 2:
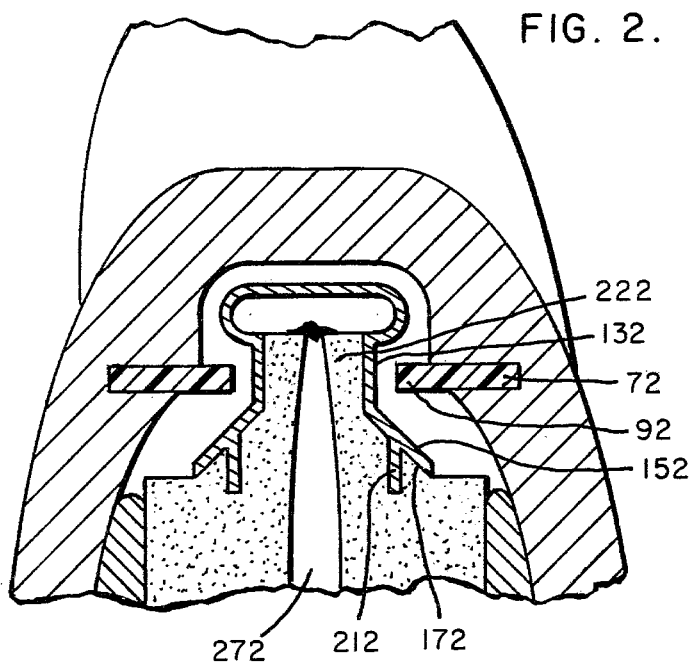
FIG. 2 is an enlarged cross-sectional view in a vertical plane of a somewhat modified form of the male, or stud, element that may be used, and a modified female element that may be used.

In FIG. 2 the constricted mid-region 132 is cylindrical, and the female element 52, of elastic material, as some form of plastic, has the general shape of a washer with the outer periphery 72 firmly secured in the denture material and the inner periphery 92, corresponding to the skirt portion 9 of FIG. 1. The inner diameter of the inner periphery of the female element 52 is larger than the outer diameter of the mid-region 132 of the male element, so that a loose fit is provided for the parts, and so that the denture gets some support from the gums as well as the tooth and jaw bone.

The lower or flange portion of the cap includes the upper surface 152, the lower surface 172, and the pins 212. The lower surface is substantially in the shape of a truncated cone, a frustum of a cone, with the surface sloping outwardly and downwardly from the apex of the tooth.

The pins 212 have the same function as the pins 21 disclosed under FIG. 1; namely, the pins 212 which are cemented into the anchor tooth not only effectively prevent rotation of the cap on the tooth but also provide a firm attachment of the cap to the tooth so that any tension applied to the cap, during removal of the denture from the cap, does not cause the cap to pull loose from the tooth, and that any lateral forces applied to the cap do not cause the interior tooth structure to fracture.

Just how many pins 212 are to be used will depend mostly on the size of the anchor tooth. The number of pins 212 used may vary from one to more than four.

Figure 3:
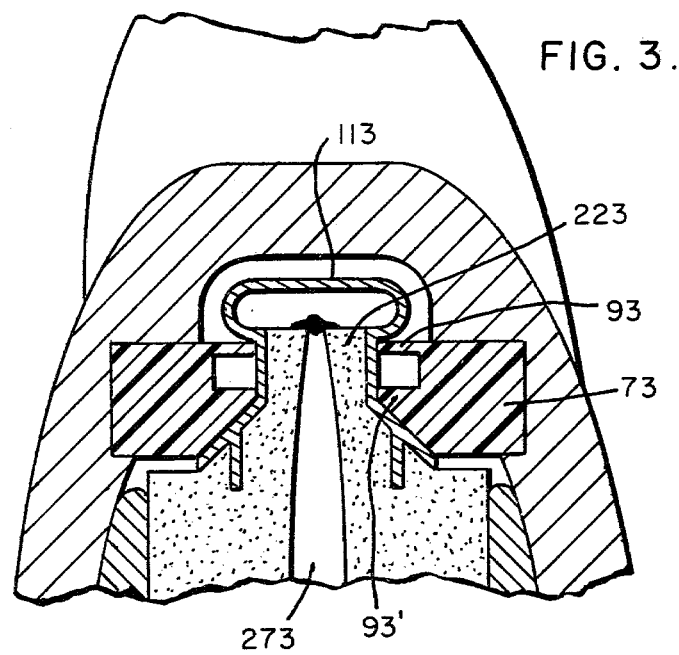
FIG. 3 is an enlarged cross-sectional view similar to the showing in FIG. 2, but where the female element is so selected and shaped that a much less resilient anchorage is provided for the denture.

In FIG. 3 the only part modified from the showing in FIG. 2 is the elastic member. This elastic member 73 may be of a more rigid material than the one shown in FIG. 2, but it could be of the same type of material. The important part of the structure of 73 is that it fits rather snugly on the cylindrical portion of the stud element. The two ring portions 93 and 93¹ facilitate passing the stud element through the elastic female element, and allow very little play neither vertically nor laterally of the denture on the stud.

The showing in FIG. 3 is especially of value when there are several good anchor teeth available so that the load during use of the denture can be placed mainly or directly on the anchor teeth.

Having fully described and shown the invention to be protected by United States Letters Patent, the inventor claims:

1. In combination, an assembly of elements for removably securing a denture in the mouth of a person who needs to wear a denture, comprising a tooth cap having a selected bottom contour so that the cap may be securely cemented to a prepared surface on the outer end of an anchor tooth, the prepared surface on the anchor tooth being made to accurately match the selected contour on the cap, said cap including, a stud element, having a head portion and a narrow neck portion, projecting from the tooth cap in a direction away from the anchor tooth, an elastic member having a ring portion with an internal diameter less than the head portion of the stud element but slightly greater than the neck portion of the stud element, so that the elastic member may be forced over the head portion to the neck portion and thus be held in place, the denture material above the head of the stud element being hollowed out sufficiently so that the pressure load on the dentures during use is not transferred to the head of the stud element, means for securing the outer region of the elastic member to the denture, the tooth cap also including, at its lower outer peripheral region, a ring portion in the shape of a frustum of a cone having an upper load receiving surface during use engaging the bottom of the ring portion of the elastic member to thus during use take some of the denture load on the gums onto the shoulder region of the anchor tooth, the ring portion of the cap also having a lower surface in the shape of the frustum of a cone to thus, when cemented to the matching surface on the anchor tooth, firmly circumferentially grips the anchor tooth to strengthen the anchor tooth against splitting.

2. The device of claim 1, wherein the anchor tooth at the prepared surface is provided with a projection surrounding the pulp canal of the tooth and the stud element is hollowed out centrally to receive, with a fit, the peripheral region of the projection in the prepared surface, but where the hollowed out depth is greater than the height of the projection in the prepared surface so as not to interfere with any medicated closure material of the pulp canal, and wherein a plurality of pins are rigidly secured to the region of the lower surface in the cap having the shape of a frustum of a cone, said pins being directed in the same general direction as the pulp canal and fit in matching holes in the shoulder region of the anchor tooth.

3. In combination, an assembly of elements for removably securing a denture in the mouth of a person who needs to wear a denture, comprising a rigid tooth cap having a selected contour at the bottom surface, namely, the surface that faces the anchor tooth selected for anchorage of the denture, said anchor tooth being provided, at the surface facing the cap, with a contour matching the said selected contour on the cap, so that the anchor tooth and cap may be securely cemented to each other, said cap having a stud element projecting away from the anchor tooth and at its outer peripheral region being shaped substantially like the surface of a truncated cone sloping over the shoulder region of the anchor tooth toward the periphery of the anchor tooth, the matching contour on the anchor tooth is provided with a projection surrounding the outer end of the pulp canal, and the stud element is hollowed out centrally to receive, with a snug fit, the peripheral region of the projection on the anchor tooth, but the hollowed out depth in the stud element is greater than the height of the projection on the anchor tooth so that the central region of the anchor tooth does not, during use of the denture, ever engage the end of the hollowed out region in the stud element, an elastic member, in the shape of an annulus, at its outer periphery firmly secured in the denture material and at the inner region engaging the rigid tooth cap at the outer surface of the projecting stud element and also engaging the top surface on the rigid tooth cap having the shape of a truncated cone, so that, during use of the denture, any pressure load relieved from the gums, is transmitted to the shoulder region of the anchor tooth.

4. The device of claim 3, wherein the rigid tooth cap is provided with a pin at the surface facing the anchor tooth in the region shaped like the surface of truncated cone, that fits into a matching hole in the anchor tooth.

* * * * *